(12) United States Patent
Wagner et al.

(10) Patent No.: US 10,890,536 B2
(45) Date of Patent: Jan. 12, 2021

(54) GEMSTONE HANDLING AND ANALYSIS SYSTEM

(71) Applicant: GemEx Systems, Inc., Mequon, WI (US)

(72) Inventors: Randall M. Wagner, Mequon, WI (US); Kurt P. Schoeckert, Hartford, WI (US)

(73) Assignee: GemEx Systems, Inc., Mequon, WI (US)

( * ) Notice: Subject to any disclaimer, the term of this patent is extended or adjusted under 35 U.S.C. 154(b) by 98 days.

(21) Appl. No.: 16/106,666

(22) Filed: Aug. 21, 2018

(65) Prior Publication Data

US 2019/0056330 A1 Feb. 21, 2019

Related U.S. Application Data

(60) Provisional application No. 62/547,978, filed on Aug. 21, 2017.

(51) Int. Cl.
*G01N 21/87* (2006.01)
*G01N 21/01* (2006.01)
(Continued)

(52) U.S. Cl.
CPC ............. *G01N 21/87* (2013.01); *B08B 1/00* (2013.01); *B08B 1/002* (2013.01); *B08B 3/04* (2013.01);
(Continued)

(58) Field of Classification Search
CPC ...................................................... G01N 21/87
(Continued)

(56) References Cited

U.S. PATENT DOCUMENTS

| 5,193,685 A | 3/1993 | Trevithick |
| 6,239,867 B1 | 5/2001 | Aggarwal |

(Continued)

OTHER PUBLICATIONS

Search report and written opinion dated Oct. 29, 2018 from related PCT Application No. PCT/US2018/04273.

(Continued)

*Primary Examiner* — Tarifur R Chowdhury
*Assistant Examiner* — Omar H Nixon
(74) *Attorney, Agent, or Firm* — Nicholas A. Kees; Godfrey & Kahn, S.C.

(57) ABSTRACT

A gemstone cleaning and analysis system and a method for cleaning and analyzing one or more gemstones using the system. The system includes a platform and an automated positioning system connected to the platform. The automated positioning system selects a gemstone from a plurality of gemstones, deposits the gemstone onto a cleaning stand connected to the platform, cleans at least one side of the gemstone by rubbing at least one side of the gemstone with at least one cleaning tool, and moves the gemstone to a gemstone imaging device connected to the platform. The gemstone imaging device has a plate, and the automated positioning system deposits the gemstone onto the plate. The gemstone imaging device identifies the gemstone. The automated positioning system moves the gemstone to a holding plate that is connected to the platform and deposits the gemstone at a particular location of the holding plate.

7 Claims, 16 Drawing Sheets

(51) Int. Cl.
  *B08B 3/04* (2006.01)
  *B08B 1/00* (2006.01)
  *G01N 33/38* (2006.01)
  *G01N 35/00* (2006.01)
  *G01N 35/04* (2006.01)
  *B25J 15/00* (2006.01)
  *G01N 21/13* (2006.01)
  *G01N 1/34* (2006.01)
  *B25J 11/00* (2006.01)
  *B25J 21/00* (2006.01)
  *B25J 19/02* (2006.01)

(52) U.S. Cl.
  CPC ....... *B25J 11/0065* (2013.01); *B25J 15/0066* (2013.01); *B25J 19/023* (2013.01); *B25J 21/00* (2013.01); *G01N 1/34* (2013.01); *G01N 21/01* (2013.01); *G01N 21/13* (2013.01); *G01N 33/381* (2013.01); *G01N 35/0099* (2013.01); *G01N 35/04* (2013.01); *G01N 2021/0187* (2013.01)

(58) Field of Classification Search
  USPC .......................................................... 356/30
  See application file for complete search history.

(56) References Cited

U.S. PATENT DOCUMENTS

| | | |
|---|---|---|
| 6,866,461 B2 | 3/2005 | DeWinter |
| 2005/0005642 A1 | 1/2005 | Kaplan |
| 2008/0231833 A1 | 9/2008 | Shlezinger |
| 2010/0155195 A1 | 6/2010 | Marchi |
| 2010/0250201 A1* | 9/2010 | Sivovolenko ......... G01N 21/88 703/1 |
| 2014/0119613 A1 | 5/2014 | D'Gama |
| 2016/0139058 A1 | 5/2016 | Patel |
| 2017/0132867 A1 | 5/2017 | Pharmadva |

OTHER PUBLICATIONS

Search report and written opinion dated Oct. 29, 2018 from related PCT Application No. PCT/US2018/047273.

* cited by examiner

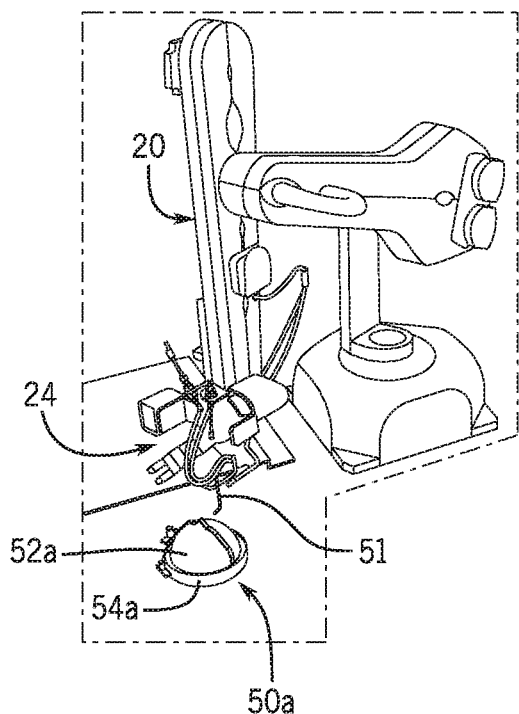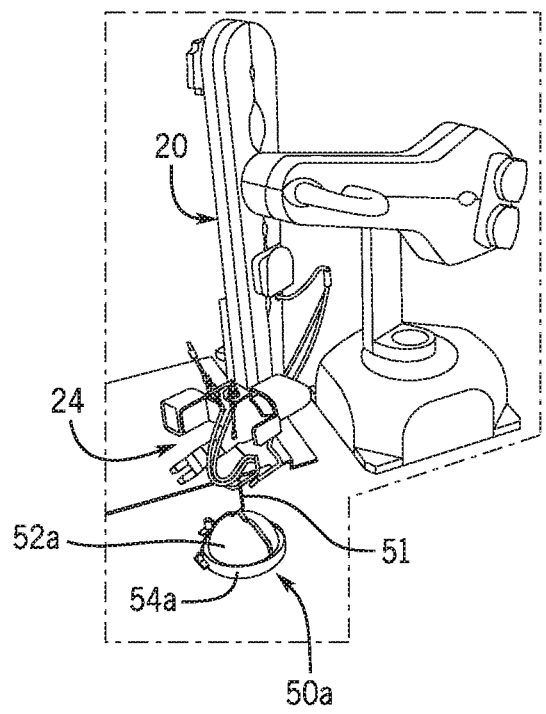
FIG. 3  FIG. 3A
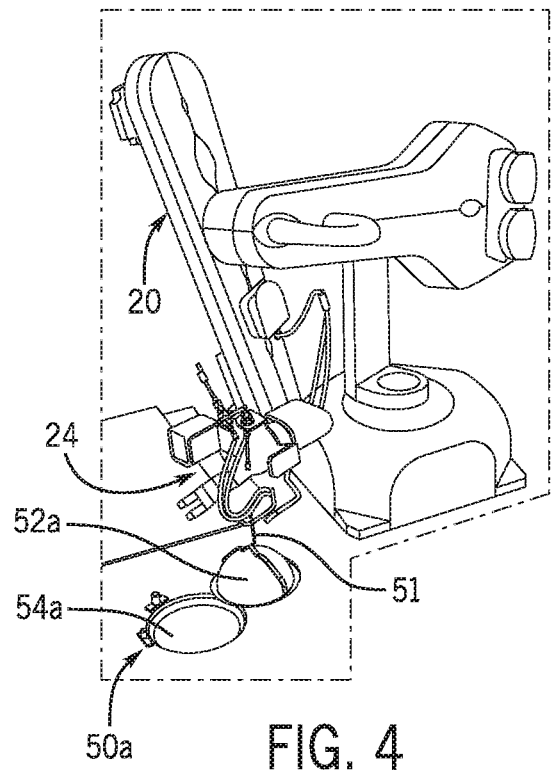
FIG. 4

GEMSTONE HANDLING AND ANALYSIS SYSTEM

CROSS REFERENCE TO RELATED APPLICATION

This application claims the benefit of U.S. Provisional Patent Application Ser. No. 62/547,978 filed Aug. 21, 2017. All of the information disclosed in that application is hereby incorporated herein by reference in its entirety.

FIELD OF THE INVENTION

The present invention relates to the field of gemstones and jewelry, and in particular to systems for handling and analyzing gemstones with security and ease of repeatability.

BACKGROUND

Due to the large intrinsic value and small size of gemstones, it has long been difficult to ensure security and repeatability in terms of handling, analyzing, and identifying gemstones. One can classify and identify one particular gemstone, but scaling up the volume of gemstones handled increases the risk that one or several of the gemstones already identified and evaluated may be swapped out for lesser stones. Additionally when gemstones are cleaned and analyzed by hand, the process is timely and introduces further risk of human error.

This invention relates to improvements to existing systems and to solutions to some of the issues raised or not solved thereby.

SUMMARY

The present disclosure relates to a system for handling and analyzing one or more gemstones. According to one aspect of the present disclosure, a gemstone handling and analysis system capable of cleaning and analyzing one or more gemstones includes a platform, a plurality of stations positioned about the platform, and an the automated positioning system capable of moving each of the one or more gemstones among the plurality of stations and automating tasks at one or more of the plurality of stations. The plurality of stations and the automated positioning system are connected to the platform. The plurality of stations includes a cleaning station, a gemstone imaging station, and a holding plate capable of holding each of plurality of the gemstones at a particular location. The cleaning station includes a stand that is sized to receive a gemstone. The gemstone imaging station includes a gemstone imaging device capable of identifying each of a plurality of the gemstones.

According to another aspect of the present disclosure, a gemstone repository includes a low-friction support surface capable of supporting a plurality of gemstones and a slidable gemstone uprighting mechanism, positioned to, at least in part, slide over the support surface when in use. The low-friction support surface includes at least one ridge.

According to another aspect of the present disclosure, a cleaning system includes a platform and an automated positioning system. The platform supports a plurality of components, including a cleaning stand and a reservoir housing a gemstone cleaning solution. The automated positioning system includes a mechanism capable of selecting, moving, and releasing a gemstone and at least one cleaning tool capable of cleaning at least one side of the gemstone.

According to another aspect of the present disclosure, the gemstone handling and analysis system includes a platform and a plurality of stations, each station positioned on the platform. The plurality of stations include a gemstone repository, a cleaning station for cleaning at least one side of each of at least some of the gemstones, a gemstone imaging station, a scale capable of weighing a gemstone, a gemstone color analyzer capable of determining a color grade for a gemstone, a gemstone clarity analyzer capable of determining a clarity grade for a gemstone, a gemstone origin analyzer capable of authenticating a gemstone, and a holding plate capable of holding gemstones in a particular location. The cleaning station has a rotatable cleaning stand capable of accepting a gemstone and a reservoir holding a gemstone cleaning solution. The gemstone imaging station includes a gemstone imaging device capable of performing a light return analysis on a gemstone, a plate attached to the gemstone imaging device, and a removable cover capable of at least partially covering the plate. The plate is sized to receive a gemstone to be analyzed. A robotic arm is further connected to the platform. The robotic arm has a gemstone gripper tool capable of selecting, moving, and depositing a gemstone and at least one tool capable of performing a cleaning function on at least one surface of a gemstone. The gemstone handling and analysis system additionally includes a plurality of external panels at least partially surrounding the platform and supported by a frame. At least one of the external panels is openable, and a locking mechanism attaches to one or more of the openable panels. The gemstone handling and analysis system further includes an input mechanism capable of receiving an input associated with a particular location on the holding plate and of providing information to the robotic arm to select a gemstone positioned at the particular location on the holding plate.

According to another aspect of the present disclosure, a gemstone handling and analysis system kit includes a platform, a gemstone repository including a ridged support surface, a gemstone uprighting mechanism capable of slidably connecting to the gemstone repository, a gemstone cleaning stand, a gemstone cleaning reservoir, a gemstone cleaning solution, a gemstone cleaning tool, a gemstone imaging device having a holding plate capable of holding each a plurality of the gemstones in a particular location, and an automated positioning system capable of selecting, moving, and depositing a gemstone.

A gemstone may be cleaned and analyzed using a gemstone cleaning and analysis system that includes a platform and an automated positioning system connected to the platform according to one aspect of the present invention by using the automated positioning system to select a gemstone from a plurality of gemstones, to deposit the gemstone onto a cleaning stand connected to the platform, to clean at least one side of the gemstone by rubbing at least one side of the gemstone with at least one cleaning tool, to move the gemstone to a gemstone imaging device that is connected to the platform and has a plate, to deposit the gemstone on the plate, to move the gemstone to a holding plate that is connected to the platform, and to deposit the gemstone at a particular location of the holding plate. The gemstone is further cleaned and analyzed by using the gemstone imaging device to identify the gemstone while the gemstone is on the plate.

A gemstone may be cleaned according to another aspect of the present invention by using an automated positioning system to select a gemstone from a series of gemstones, to deposit the gemstone onto a cleaning stand connected to a platform, to wet a cleaning tool in a reservoir containing a gemstone cleaning solution, to rub at least one side of the gemstone with the cleaning tool, and to rub at least one side of the gemstone with a different cleaning tool that has not been wetted with the gemstone cleaning solution.

A plurality of gemstones may be uprighted according to another aspect of the present invention by depositing a series of gemstones onto a low-friction support surface and electrically moving a brush element that has bristles back and forth over the low friction support surface, such that the bristles contact at least some of the gemstones. The low-friction support surface has at least one ridge, and the contact between the bristles and the gemstones causes at least a portion of the gemstones to move and interact with the ridge.

A gemstone may be cleaned and analyzed using a gemstone cleaning and analysis system that includes a platform and an automated positioning system connected to the platform according to another aspect of the present invention by using the automated positioning system to select a first gemstone from a plurality of gemstones, to place the first gemstone onto a cleaning stand connected to the platform, to clean at least one side of the first gemstone by rubbing at least one side of the first gemstone with at least one cleaning too, to at least partially remove a gemstone imaging device cover from a first gemstone imaging device connected to the platform, exposing at least part of a plate of the first gemstone imaging device, to deposit the first gemstone onto the plate of the first gemstone imaging device, and to replace the gemstone imaging device cover of the first gemstone imaging device. The first gemstone imaging device is used to perform a light return analysis on the first gemstone. Additionally, the automated positioning system is used to select a second gemstone from the plurality of gemstones, to place the second gemstone onto the cleaning stand, to clean the second gemstone by rubbing at least one side of the second gemstone with one or more polishing tools, to at least partially remove a gemstone imaging device cover from a second gemstone imaging device connected to the platform, exposing at least part of a plate of the second gemstone imaging device, to place the second gemstone onto the plate of the second gemstone imaging device, and to replace the gemstone imaging device cover of the second gemstone imaging device. The second gemstone imaging device is used to perform a light return analysis on the second gemstone. The automated positioning system is further used to at least partially remove the gemstone imaging device cover of the first gemstone imaging device, to move the first gemstone to a first location on a holding plate, to at least partially remove the gemstone imaging device cover of the second gemstone imaging device, and to move the second gemstone to a second location on the holding plate.

Other objects and advantages of the present disclosure will become apparent hereinafter.

DESCRIPTION OF THE DRAWING

FIG. 3 is an enlarged perspective view of a different portion of the system shown in FIG. 2.

FIG. 3A is another enlarged perspective view of the portion of the system of FIG. 2 shown in FIG. 3, showing certain components in different positions.

FIG. 4 is another enlarged perspective view of the portion of the system of FIG. 2 shown in FIG. 3, showing certain components in different positions.

DETAILED DESCRIPTION

Figure 1:
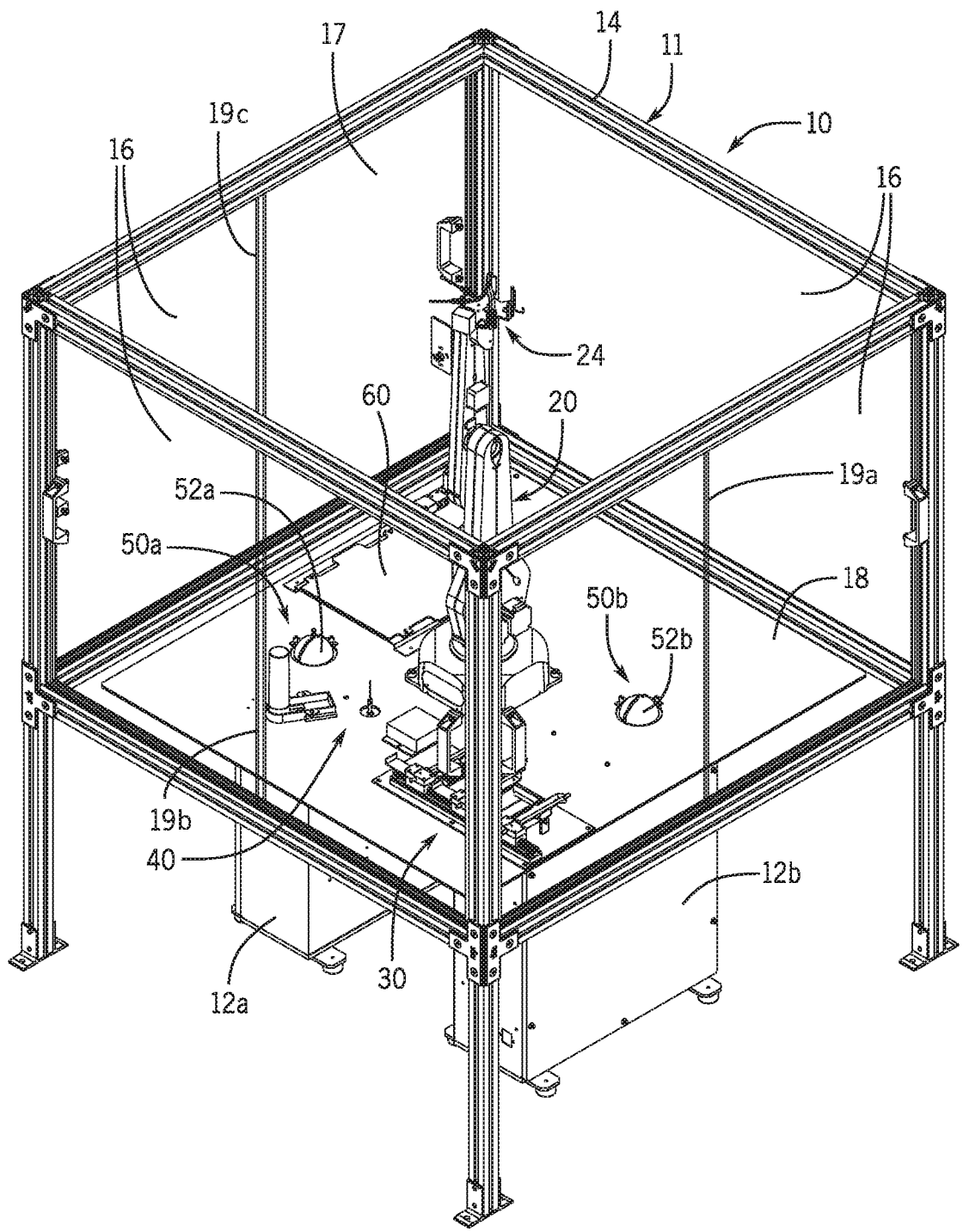
FIG. 1 is an isometric view of a gemstone handling and analysis system constructed according to one embodiment of the invention.

Referring now to FIG. 1, there is shown a gemstone handling and analysis system 10 constructed according to one embodiment of the present invention. In this embodiment, the system 10 includes an enclosure 11 surrounding a platform 18. In the embodiment shown, the enclosure 11 includes a frame 14. The frame 14 supports side panels 16, enclosing the platform 18, and a top panel 17, positioned above the platform 18. Certain embodiments could also include a bottom panel that supports the platform 18. In the embodiment shown, the platform 18 is supported within the enclosure 11 by other means, as will be described more fully below. A small gap 18a may exist between the edges of the platform 18 and the side panels 16, but any such gap must be small enough, such as one inch or less, that a person could not reach through such a gap and access the platform without authority to do so.

The side panels 16 and top panel 17 of the enclosure 11 may be clear, so as to permit an operator to inspect operations on the platform 18. Alternatively, the side panels 16 and top panel 17 may be opaque, so as to maintain confidentiality regarding operations on the platform 18. Preferably at least one panel of the enclosure 11 is openable. In this embodiment, each openable panel comprises two panel portions that may slide past each other and form an overlap 19. In the embodiment shown, there are three panel sets that are openable, with overlaps 19a, 19b and 19c. In some embodiments, the openable panels may additionally be lockable, at least by means of some locking mechanism, or by utilizing a detector, such as a proximity reed switch, to detect the opening of the enclosure 11. This increases security in relation to gemstone insertion and removal. Some embodiments may further include an alarm that sounds whenever one of the panels is opened, or whenever one of the panels is broken. Alternatively, some embodiments may include openable panels that are not lockable.

The system 10 includes at least one gemstone imaging device 12 positioned below the platform 18. In some embodiments the gemstone imaging devices(s) 12 support the platform 18 in position, within the enclosure 11. In certain embodiments, two or more gemstone imaging devices 12a, 12b may be included. In some embodiments, the gemstone imaging devices 12a, 12b may be Brilliance Scope® imaging devices from GemEx Systems.

Mounted on the platform 18, within the enclosure 11, is an automated positioning system 20. While any suitable system, such as a conventional X-Y positioning system, may be used, the automated positioning system 20 in the embodiment shown is a robotic arm system. The inventors have found that the Model R12 robot from ST Robotics works suitably well.

Figure 2:
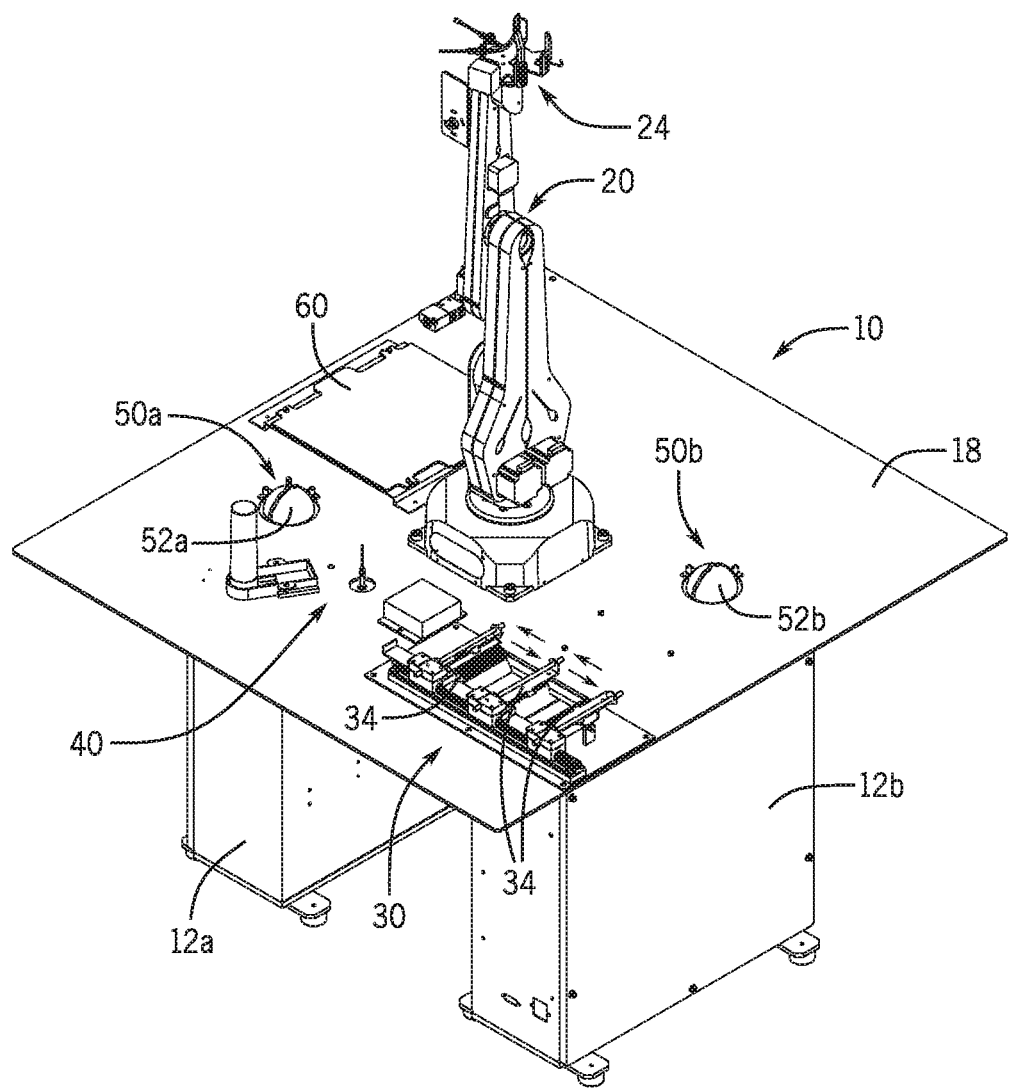
FIG. 2 is an isometric view of the gemstone handling and analysis system shown in FIG. 1, with the enclosure elements removed to show internal elements.

FIG. 2 shows the platform 18 as shown in FIG. 1, without the enclosure 11. In this embodiment, the platform 18 may include the robotic arm 20, along with a plurality of processing stations, such as a repository station 30, a cleaning station 40, gemstone imaging stations 50a, 50b, and a holding plate 60. As will be explained in further detail below, the robotic arm 20 includes a working hand 24, having several tools or elements mounted thereon, to accomplish the various tasks described herein.

The embodiment shown in FIG. 2 may include two gemstone imaging stations 50a, 50b. This allows one gemstone to be analyzed at the first gemstone imaging station 50a while another gemstone is cleaned and taken to the second gemstone imaging station 50b for analysis. In other embodiments, more or fewer gemstone imaging stations may be included. As shown in FIG. 2, the platform 18 may also include a repository station 30. In addition to the processing stations shown in FIG. 2, FIGS. 21-24 schematically depict examples of further processing stations that the platform 18 may include, such as a scale 70, a gemstone color analyzer 80, a gemstone clarity analyzer 90, and/or a gemstone origin analyzer 100.

FIGS. 2A-25 illustrate the processing stations in further detail, as the system carries out various processes. FIGS. 3-4 show a first gemstone imaging station 50a. In FIG. 3, the robotic arm 20, carrying a hook element 51, moves towards a cover 52a of the first gemstone imaging device 12a. FIG. 3A then shows the robotic arm 20 using the hook element 51 to remove the cover 52a, revealing a plate 54a of the first gemstone imaging device 12a (FIG. 2). In the embodiment shown, when removing the cover 52a, the hook element 51 interacts with a loop formed on the cover 52a. In FIG. 4, the robotic arm 20 sets aside the cover 52a, leaving at least part of the plate 54a exposed and ready to accept a gemstone for analysis.

Figure 2A:
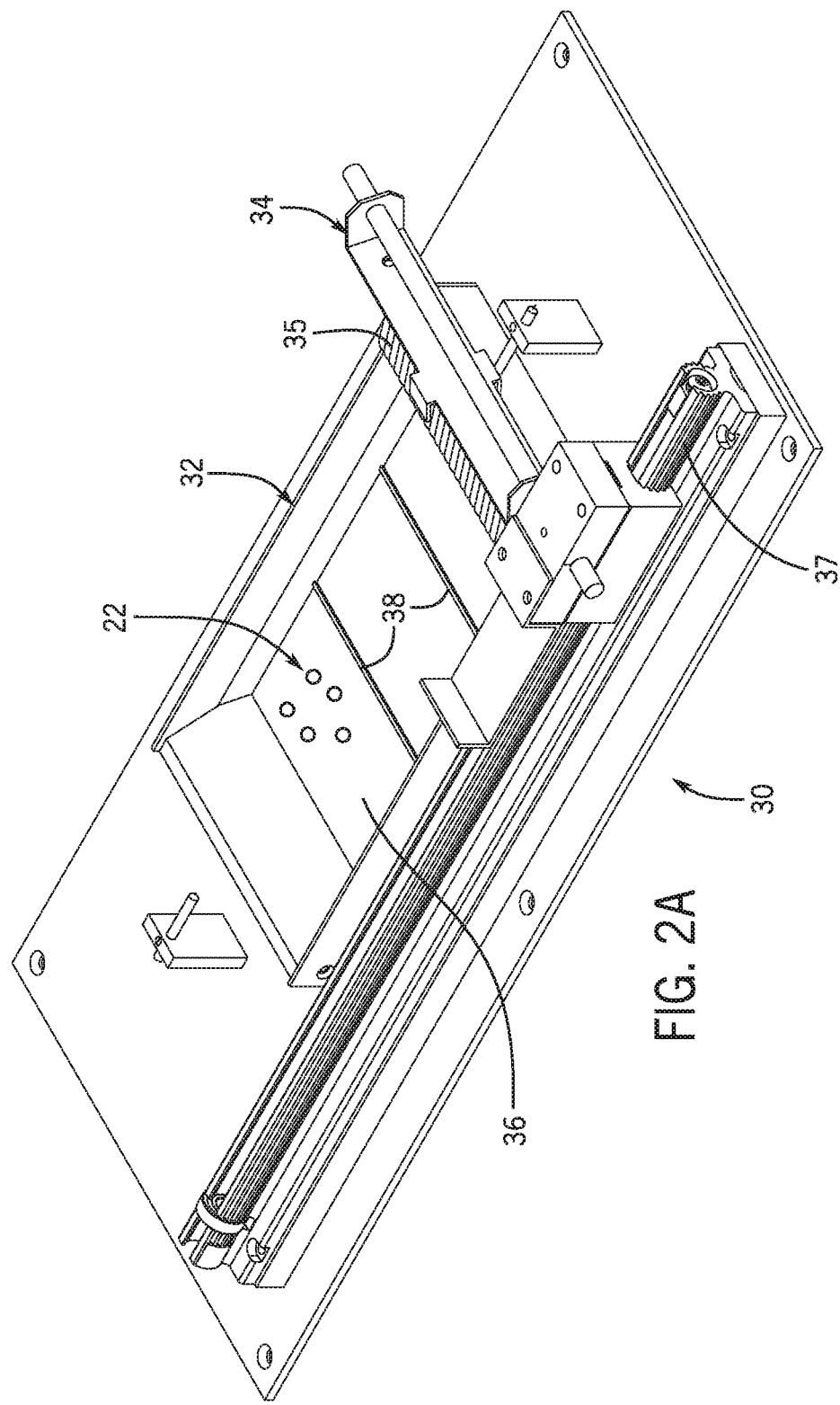
FIG. 2A is an enlarged isometric view of a portion of the system shown in FIG. 2.

FIG. 2A shows an enlarged view of the repository station 30 where, in this embodiment, a series of gemstones 22 are first deposited upon entering the system 10. The repository station 30 includes an initial repository 32 having a support surface 36 for receiving the gemstones 22. In the embodiment shown, the repository station 30 may further include an uprighting mechanism 34. In this embodiment, the uprighting mechanism 34 is a brush element having soft bristles 35. The uprighting mechanism 34 slidably connects to the repository station 30 via a slider track 37. The slider track 37 may attach to the platform 18 and/or to the initial repository 32. In other embodiments, other forms of uprighting mechanisms or attachment means that permit back-and-forth movement over the support surface 36 may suffice, such as a linear motor or other type of motor. In this embodiment, the support surface 36 is comprised of a non-reflective, low-friction material, such as anodized aluminum. The support surface 36 may further include one or more raised ledges or ridges 38 that may aid in the uprighting process. In the embodiment shown, when in use, the uprighting mechanism 34 is moved by a tab tool 39 of the robotic arm 20, back and forth over the support surface 36 at a height such that contact between the bristles 35 and the gemstones 22 causes the gemstones 22 to move and interact with the raised ledges or ridges 38.

Figure 5:
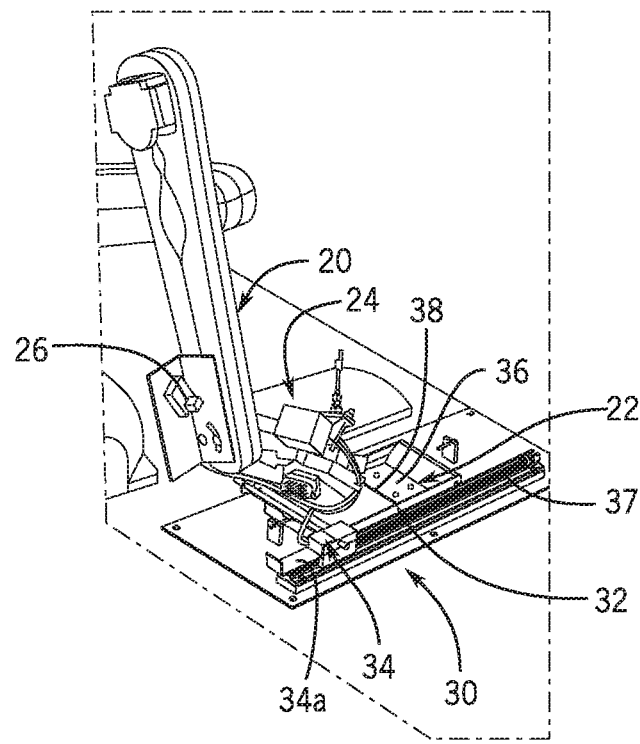
FIG. 5 is an enlarged perspective view of a different portion of the system shown in FIG. 2.
Figure 6:
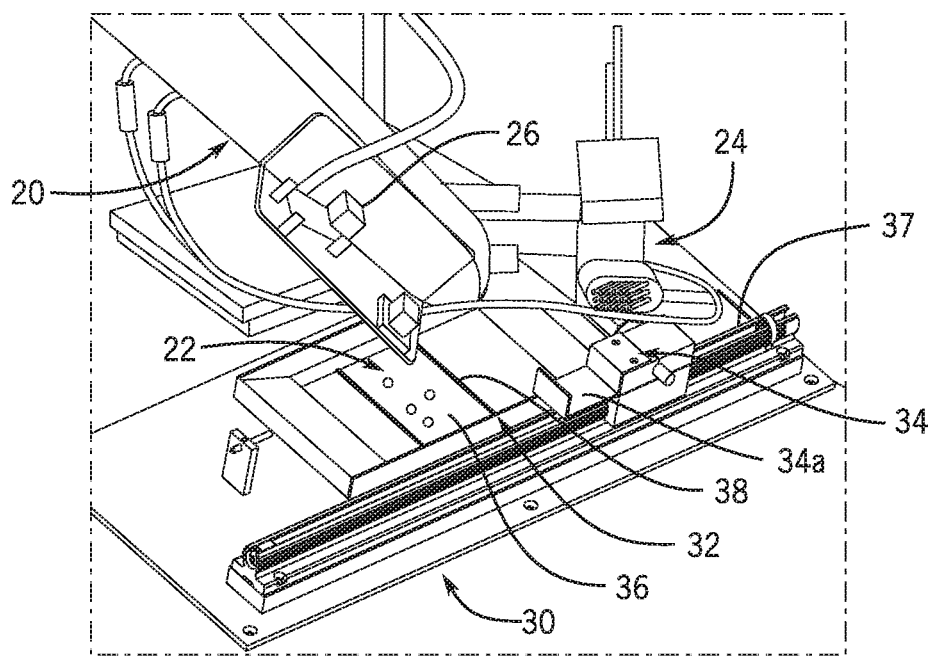
FIG. 6 is another enlarged perspective view of the portion of the system of FIG. 2 shown in FIG. 5, showing certain components in different positions.
Figure 7:
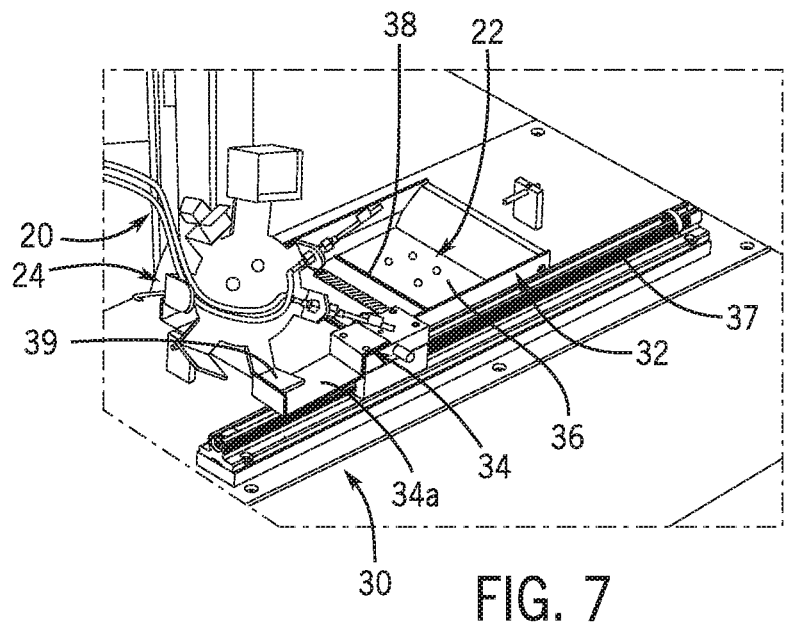
FIG. 7 is another enlarged perspective view of the portion of the system of FIG. 2 shown in FIG. 5, showing certain components in different positions.

FIGS. 5-7 show the gemstone repository station 30 as the gemstone uprighting mechanism 34 uprights the gemstones 22 deposited in the initial repository 32. In FIG. 5, the gemstones 22 are positioned on the support surface 36, each in no particular orientation, and the gemstone uprighting mechanism 34 is still in an initial position. FIG. 6 shows the position of the uprighting mechanism 34 after the robotic arm 20 moves the uprighting mechanism 34 over the gemstones 22 for the first time. In this embodiment, the robotic arm 20 moves the uprighting mechanism 34 by fitting the tab tool 39 into a slot 34a of the uprighting mechanism 34 and moving the tab tool 39 in a direction that pushes the uprighting mechanism 34 over the support surface 36 along the slider track 37. Subsequently, the tab tool 39 pulls the uprighting mechanism 34 back over the support surface 36, as shown in FIG. 7. As the uprighting mechanism 34 moves back and forth over the gemstones 22, the bristles 35 of the uprighting mechanism 34 cause the gemstones 22 to move and come into contact with the raised ridges 38. In this embodiment, the interaction between the bristles 35, the gemstones 22, and the raised ridges 38 tends to reorient the gemstones 22 to their most stable position—table side down, pavilion side up, and the culet at the highest point.

Figure 7A:
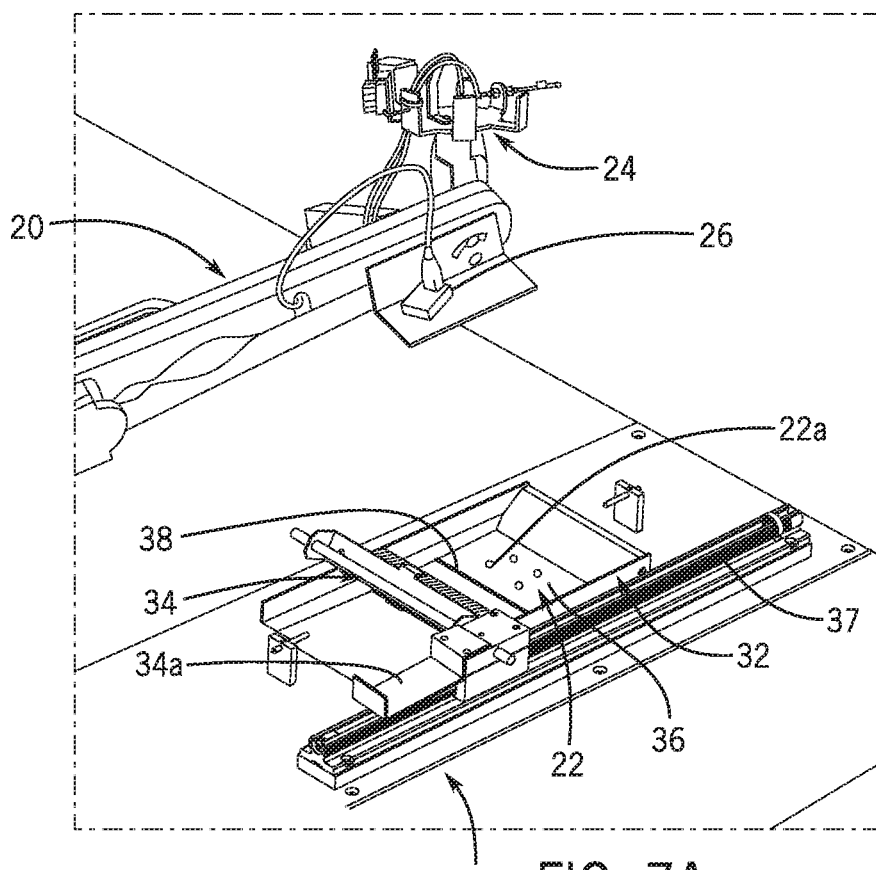
FIG. 7A is another enlarged perspective view of the portion of the system of FIG. 2 shown in FIG. 5, showing certain components in different positions.
Figure 7B:
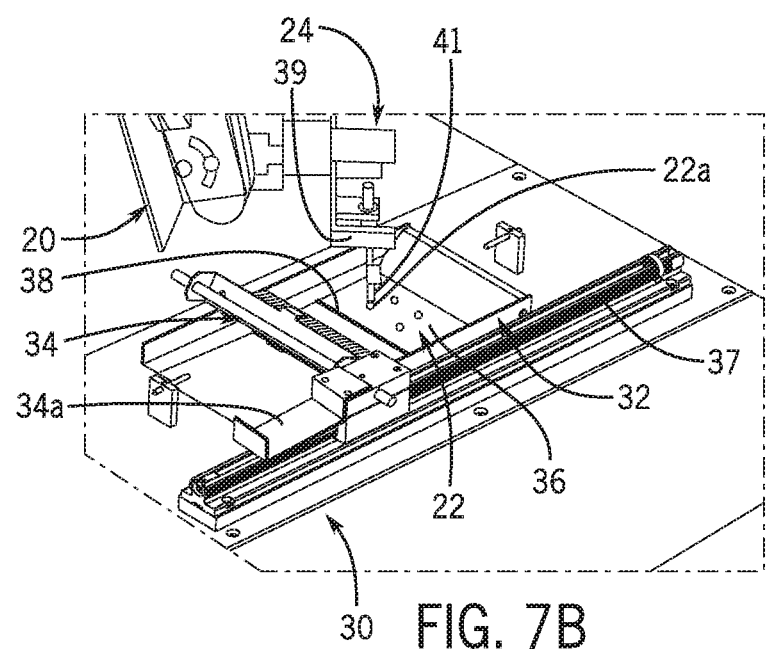
FIG. 7B is another enlarged perspective view of the portion of the system of FIG. 2 shown in FIG. 5, showing certain components in different positions.

In the embodiment shown, once the uprighting mechanism 34 has operated a first time, the robotic arm 20 moves to the position shown in FIG. 7A. In that position, a camera 26 attached to the robotic arm 20 views the gemstones and determines which ones are in the upright position, along with the location of each such upright gemstone. By means of a gemstone gripper tool 41, robotic arm 20 picks up a first upright gemstone 22a from the initial repository 32, as shown in FIG. 7B, for processing as described below. Once all upright gemstones have been picked up, the uprighting mechanism 34 may be operated again, to upright more of the gemstones, which are then taken by the gemstone gripper tool 41 for processing. This part of the process happens iteratively until there are no more stones on the support surface 36.

Figure 8:
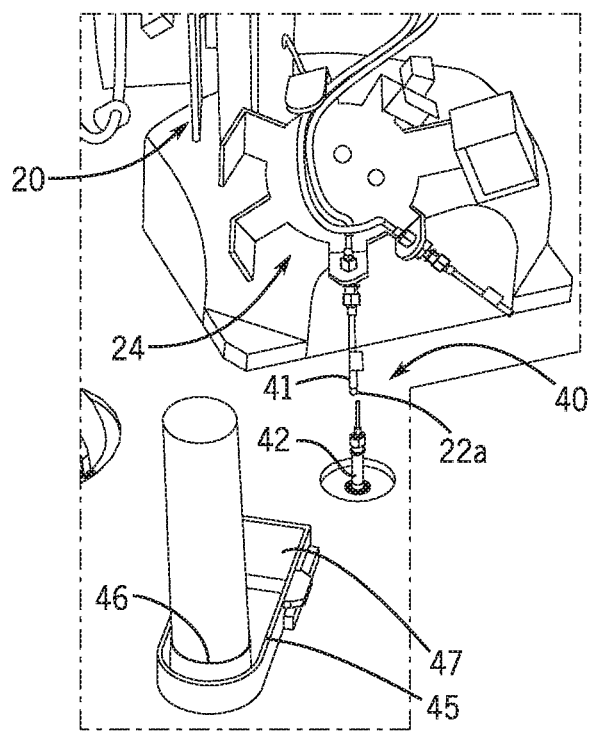
FIG. 8 is an enlarged perspective view of a different portion of the system shown in FIG. 2.
Figure 9:
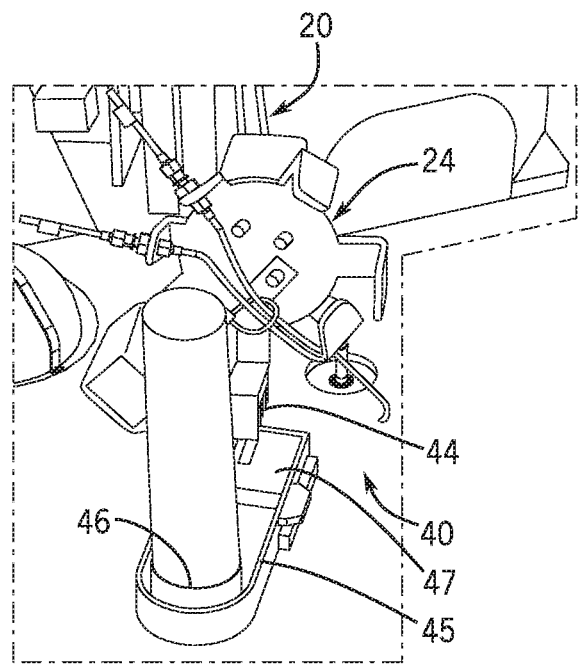
FIG. 9 is another enlarged perspective view of the portion of the system of FIG. 2 shown in FIG. 8, showing certain components in different positions.

FIGS. 8-15 show the cleaning station 40 of the system 10. FIG. 8 shows the gemstone gripper tool 41 placing the first gemstone 22a on a cleaning stand 42. In this embodiment, the first gemstone 22a is held on the cleaning stand by means of vacuum, although other means of holding the first gemstone on the cleaning stand may be employed. The first gemstone 22a is oriented such that, when placed on the cleaning stand 42, the table side faces down on the stand and the pavilion side is exposed upward. FIG. 9 shows the robotic arm 20 with a cleaning tool 44, wetting the cleaning tool in a reservoir 45 filled with a cleaning solution 46. In practice, isopropyl alcohol is one cleaning solution that works well. In the embodiment shown, the reservoir 45 includes a sponge 47 positioned, at least partially, within the cleaning solution 46, so as to absorb the cleaning solution 46. To wet the cleaning tool 44, the robotic arm 20 presses the cleaning tool 44 into the sponge 47. Although a sponge is used in the present embodiment, other forms of absorbent materials may be used in other embodiments. Alternatively, some embodiments may utilize no absorbent material, and the robotic arm 20 may simply dip the cleaning tool 44 directly into the cleaning solution 46. In the embodiment shown in FIG. 9, the cleaning tool 44 is a brush. However, in other embodiments, the cleaning tool 44 may be a cloth or other form of cleaning tool. The important point is that the cleaning tool 44 polishes the gemstone and removes dirt and smudges.

Figure 10:
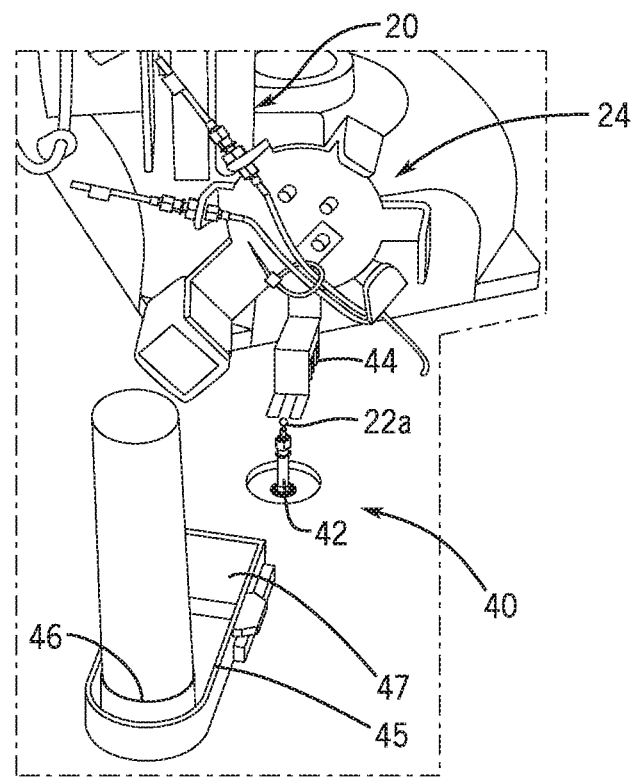
FIG. 10 is another enlarged perspective view of the portion of the system of FIG. 2 shown in FIG. 8, showing certain components in different positions.
Figure 11:
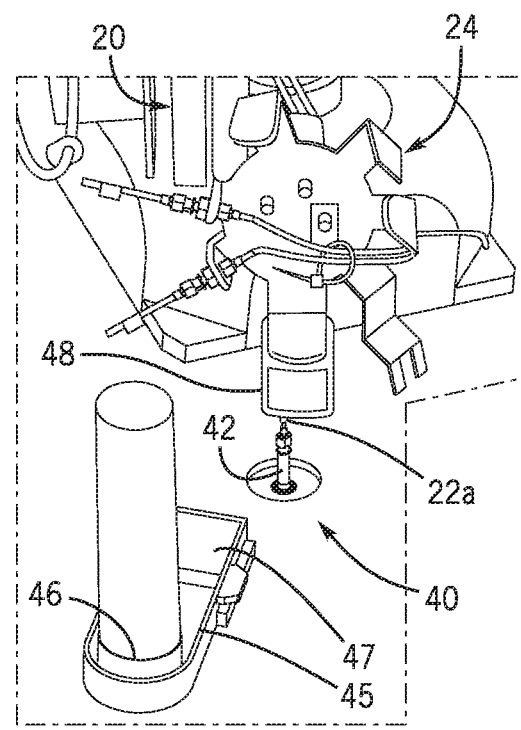
FIG. 11 is another enlarged perspective view of the portion of the system of FIG. 2 shown in FIG. 8, showing certain components in different positions.
Figure 12:
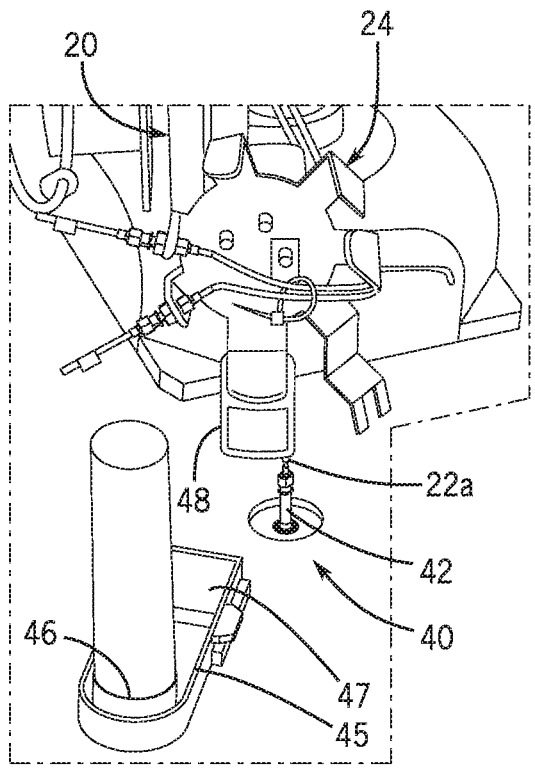
FIG. 12 is another enlarged perspective view of the portion of the system of FIG. 2 shown in FIG. 8, showing certain components in different positions.

In FIG. 10, the robotic arm 20 rubs the cleaning tool 44 against the pavilion side of the first gemstone 22a. In this embodiment, the cleaning stand 42 rotates at a suitable speed (by a suitable motor, such as a DC motor controlled by the same software that controls the robotic arm 20) as the robotic arm 20 moves the cleaning tool 44 to rub the first gemstone 22a. Alternatively, the cleaning stand 42 may remain stationary while the robotic arm 20 moves the cleaning tool 44 to rub the first gemstone 22a, or the robotic arm 20 may hold the cleaning tool 44 stationary against the pavilion side of the first gemstone 22a as the cleaning stand 42 rotates the first gemstone 22a at a suitable speed against the stationary cleaning tool 44. In this embodiment, cleaning tool 44 comprises a brush, although in other embodiments, another form of cleaning tool may be used. In FIGS. 11-12 the robotic arm 20 cleans the gemstone using a first polishing tool 48, rubbing the first polishing tool 48 against the pavilion side of the first gemstone 22a. In this embodiment, the cleaning stand 42 rotates at a suitable speed as the robotic arm 20 moves the first polishing tool 48 to rub the first gemstone 22a. Alternatively, the cleaning stand 42 may remain stationary while the robotic arm 20 moves the first polishing tool 48 to rub the first gemstone 22a, or the robotic arm 20 may hold the first polishing tool 48 stationary against the pavilion side of the first gemstone 22a as the cleaning stand 42 rotates the first gemstone 22a at a suitable speed against the (in this embodiment, stationary) first polishing tool 48. In the embodiment shown, the first polishing tool 48 comprises a cloth attached to one or more sides of a block, although in other embodiments, another form of polishing tool may be used.

Figure 13:
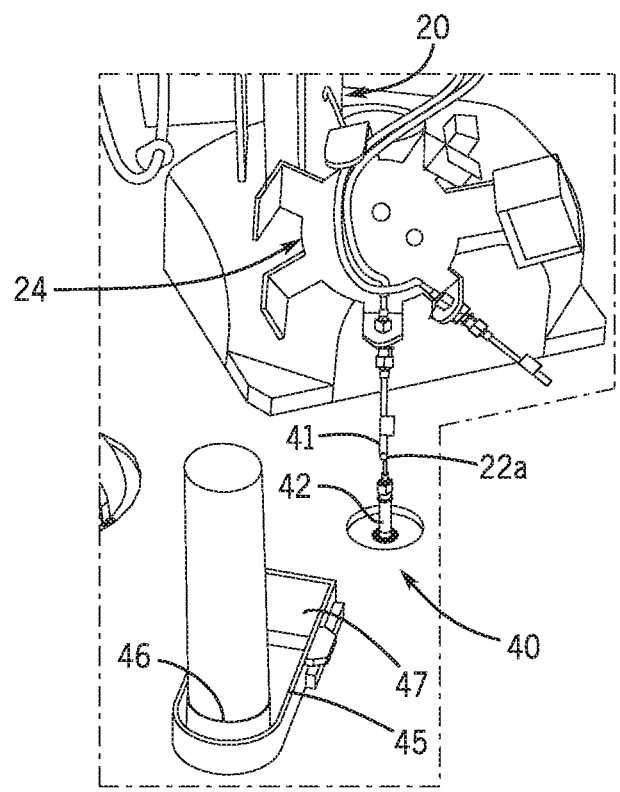
FIG. 13 is another enlarged perspective view of the portion of the system of FIG. 2 shown in FIG. 8, showing certain components in different positions.
Figure 14:
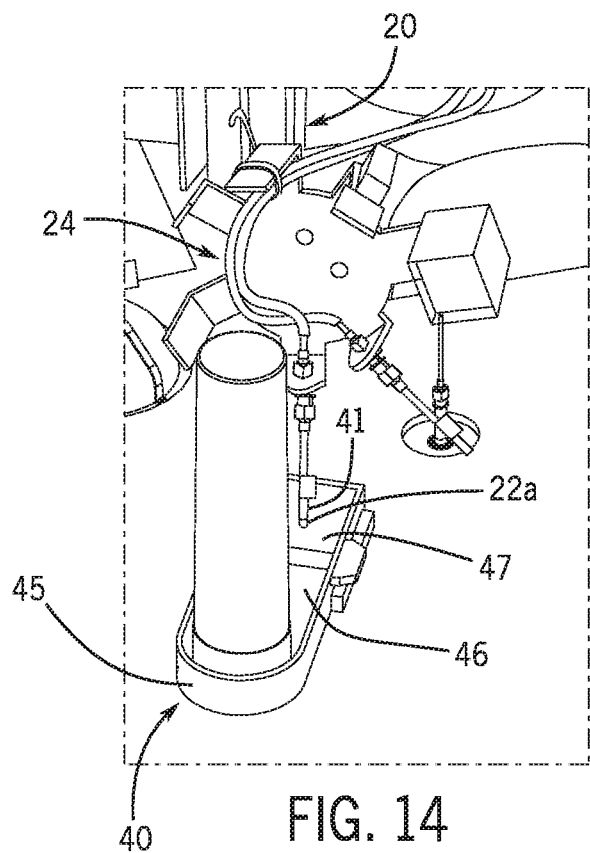
FIG. 14 is another enlarged perspective view of the portion of the system of FIG. 2 shown in FIG. 8, showing certain components in different positions.
Figure 15:
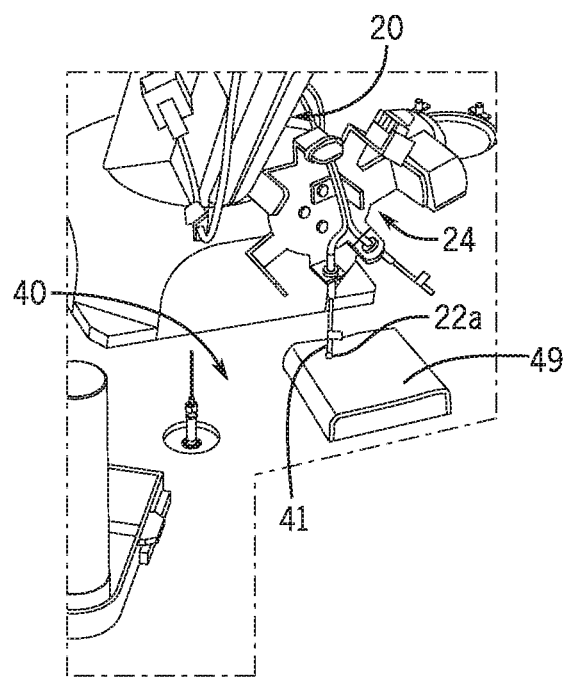
FIG. 15 is an enlarged perspective view of a different portion of the system shown in FIG. 2.

FIG. 13 shows the robotic arm 20 removing the first gemstone 22a from the cleaning stand 42 by means of the gemstone gripper tool 41. In FIG. 14, the robotic arm 20 wets the first gemstone 22a, at least the table side, in the reservoir 45 of the cleaning solution 46. To wet the first gemstone 22a, the robotic arm 20 presses the first gemstone 22a into the sponge 47. Alternatively, the robotic arm 20 may simply dip at least the table side of the first gemstone 22a directly into the cleaning solution 46. In FIG. 15, the robotic arm 20 further cleans the first gemstone 22a by rubbing at least the table side of the first gemstone 22a against a second polishing tool 49. In the embodiment shown, the second polishing tool 49 is a cloth attached to a block, the block supported by the platform 18, although in other embodiments, another form of polishing tool may be used. Notice that, in this embodiment, the gemstone is maintained in substantially the same orientation throughout the cleaning process: the table side down, the pavilion side up, and the culet at the highest point.

In alternative embodiments, the cleaning station 40 may comprise different combinations of the above described cleaning and polishing tools. For example, in situations where the gemstones 22 have been pre-cleaned in cleaning solution before entering the system 10, the steps involving cleaning the gemstones 22 with the cleaning tool 44 and the cleaning solution 46 may be eliminated. Further, where the operator anticipates commonly pre-cleaning the gemstones 22 in cleaning solution 46 before depositing the gemstones 22 into the system 10, the reservoir 45 of cleaning solution 46 and the cleaning tool 44 may be eliminated altogether from the system 10. In such an embodiment, the first polishing tool 48 and/or the second polishing tool 49 can still be used to clean the gemstones 22 in order to remove any excess dust before the analysis process begins. The cleaning process improves the quality of the gemstone imaging analysis. When the gemstone clarity analyzer 90 is included on the platform 18 and it is desired to perform a clarity grading analysis, the cleaning process may also improve the clarity grading analysis.

Figure 16:
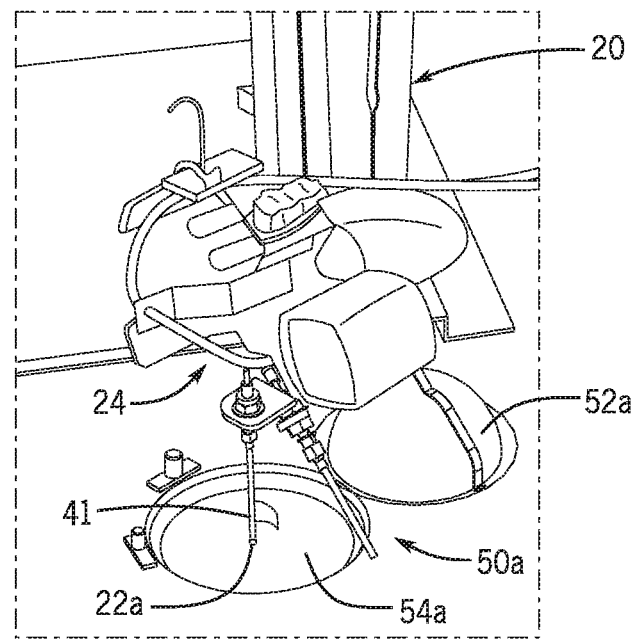
FIG. 16 is another enlarged perspective view of the portion of the system of FIG. 2 shown in FIG. 3, showing certain components in different positions.
Figure 17:
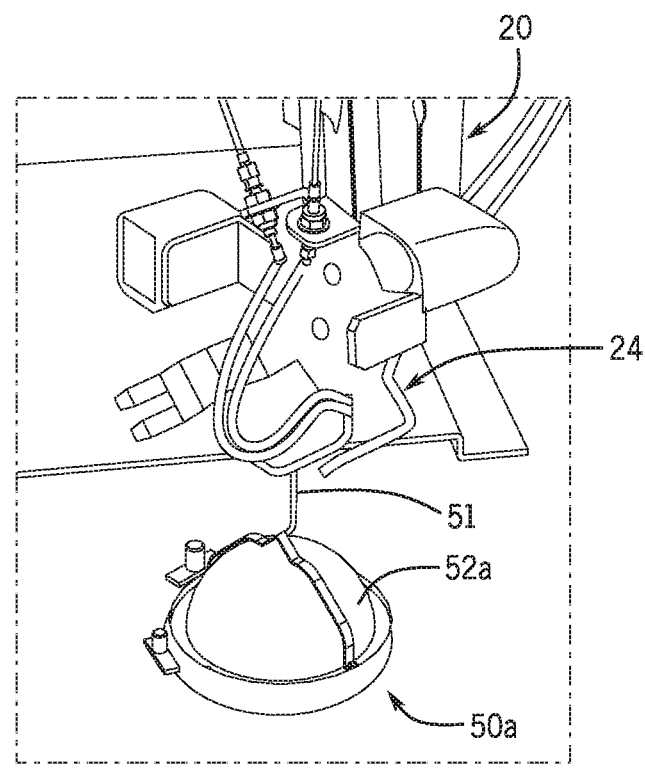
FIG. 17 is another enlarged perspective view of the portion of the system of FIG. 2 shown in FIG. 3, showing certain components in different positions.
Figure 18:
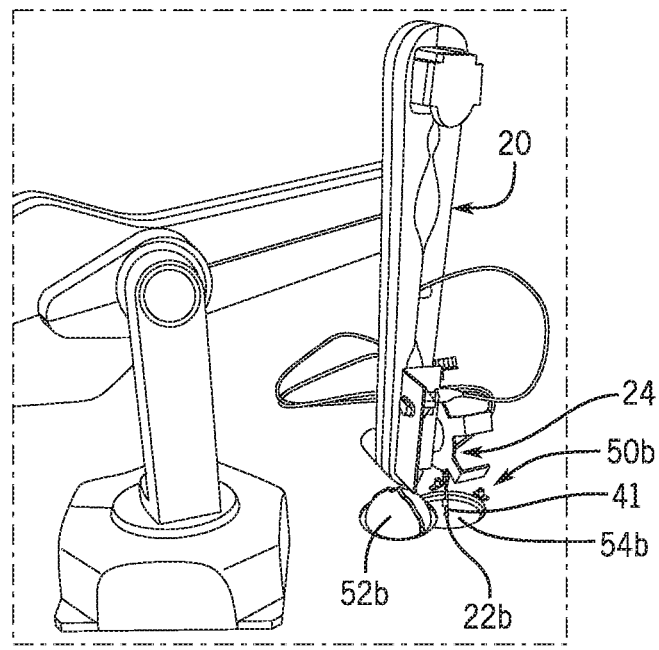
FIG. 18 is an enlarged perspective view of a different portion of the system shown in FIG. 2.
Figure 19:
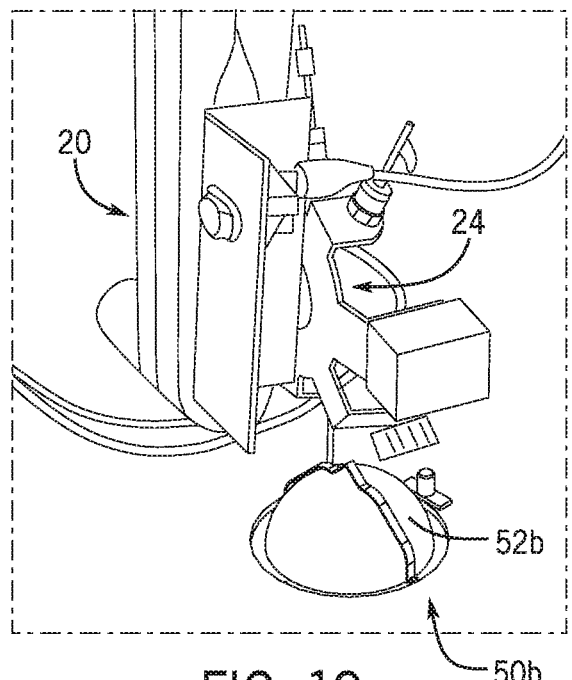
FIG. 19 is another enlarged perspective view of the portion of the system of FIG. 2 shown in FIG. 18, showing certain components in different positions.
Figure 20:
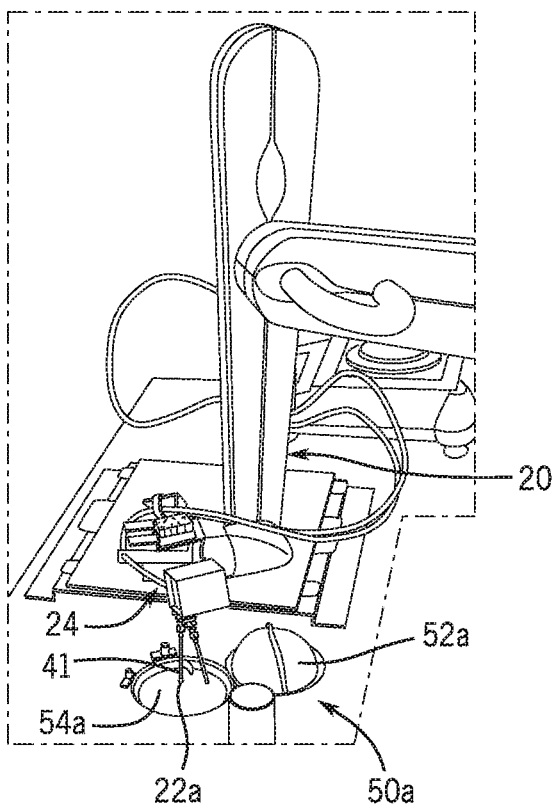
FIG. 20 is another enlarged perspective view of the portion of the system of FIG. 2 shown in FIG. 3, showing certain components in different positions.

FIGS. 16-17 show the first gemstone imaging station 50a. In FIG. 16, the robotic arm 20 places the first gemstone 22a on the plate 54a. In FIG. 17, the robotic arm 20 uses the hook element 51 to replace the cover 52a, covering the plate 54a and the first gemstone 22a. The first gemstone imaging device 12a (FIG. 2) then proceeds to perform its analysis, at least identifying the gemstone 22a by means of finding and storing an identification indicator, such as a number or set of alphanumeric characters, etched into the surface of the gemstone. While the first gemstone imaging device 12a (FIG. 2) analyzes the first gemstone 22a, the robotic arm 20 selects a second gemstone 22b from the initial repository 32, moves the second gemstone 22b to the cleaning station 40 to be cleaned in the manner described above, and then places the gemstone on a plate 54*b* of the second gemstone imaging device 12*b*, as shown in FIG. 18. In FIG. 18, a cover 52*b* has already been removed, at least partially, from the plate 54*b*. In FIG. 19, the robotic arm 20 uses the hook element 51 to replace the cover 52*b*, covering the plate 54*b* and the second gemstone 22*b*. The second gemstone imaging device 12*b* (FIG. 2) then proceeds to view and identify the second gemstone 22*b*. In certain embodiments, the system 10 further stores the information obtained from the analysis. In certain embodiments the gemstone imaging devices may also conduct a light return analysis. While the second gemstone imaging device 12*b* (FIG. 2) analyzes the second gemstone 22*b*, the robotic arm 20 returns to the first gemstone imaging station 50*a*, sets aside the cover 52*a*, and removes the gemstone 22*a*, as shown in FIG. 20.

Figure 21:
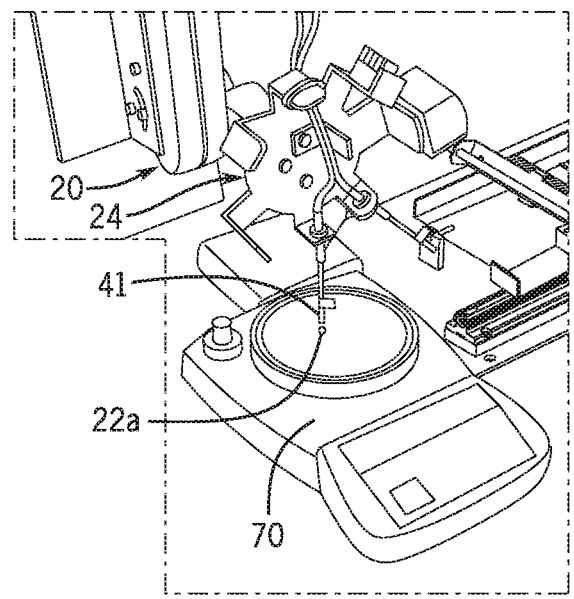
FIG. 21 is a schematic perspective view of a scale placed within a gemstone handling and analysis system constructed according to one embodiment of the invention.
Figure 22:
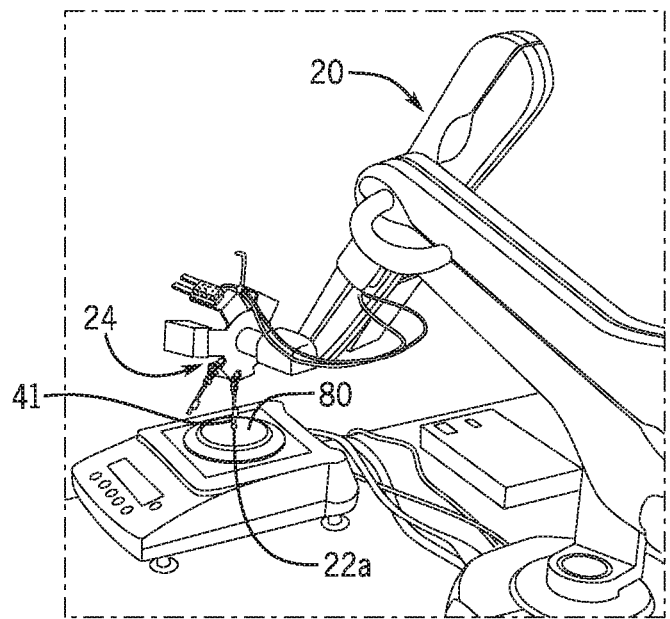
FIG. 22 is a schematic perspective view of a gemstone color analyzer placed within a gemstone handling and analysis system constructed according to another embodiment of the invention.
Figure 23:
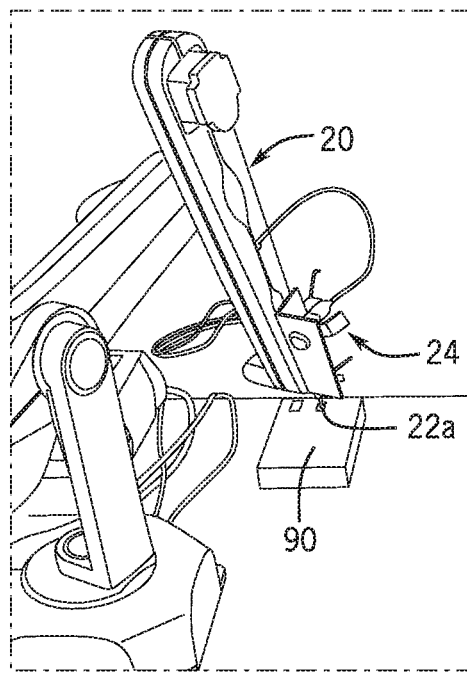
FIG. 23 is a schematic perspective view of a gemstone clarity analyzer placed within a gemstone handling and analysis system constructed according to another embodiment of the invention.
Figure 24:
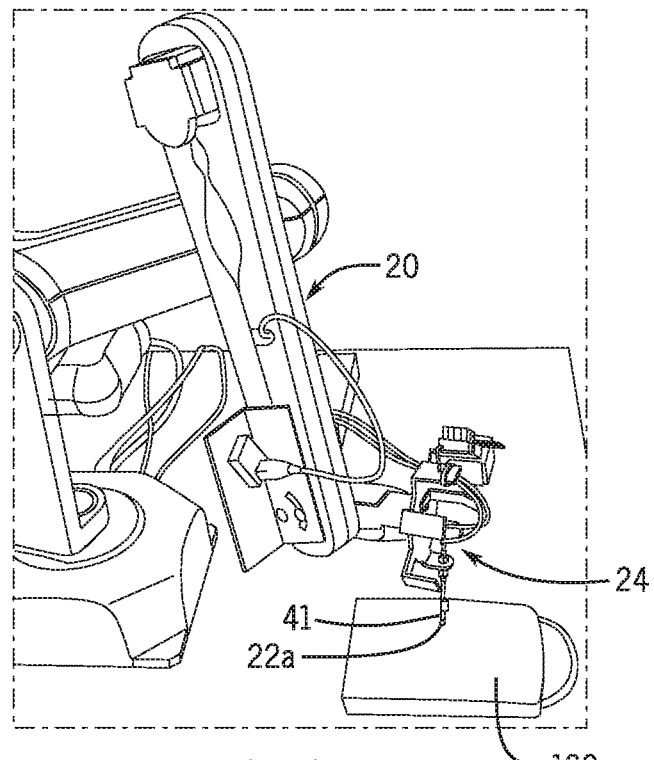
FIG. 24 is a schematic perspective view of a gemstone origin analyzer placed within a gemstone handling and analysis system constructed according to another embodiment of the invention.

In embodiments where the system 10 includes additional processing stations, the robotic arm 20 will additionally move the first gemstone 22*a* to each additional processing station for further analysis. FIG. 21 shows the robotic arm 20 placing the first gemstone 22*a* onto the scale 70, depicted schematically. The scale 70 measures the weight of the first gemstone 22*a*. In certain embodiments, the system 10 further stores the measured weight. FIG. 22 shows the robotic arm 20 placing the first gemstone 22*a* onto the gemstone color analyzer 80, again depicted schematically. The gemstone color analyzer 80 assigns a color grade to the first gemstone 22*a*. In certain embodiments, the system 10 further stores the assigned color grade. FIG. 23 shows the robotic arm 20 placing the first gemstone 22*a* onto the gemstone clarity analyzer 90, again depicted schematically. The gemstone clarity analyzer assigns a clarity grade to the first gemstone 22*a*. In certain embodiments, the system 10 further stores the assigned clarity grade. FIG. 24 shows the robotic arm 20 placing the first gemstone 22*a* onto the gemstone origin analyzer 100, again depicted schematically. The gemstone origin analyzer 100 determines whether the first gemstone 22*a* is a natural or a man-made stone. In certain embodiments, the system 10 further stores the determination.

Figure 25:
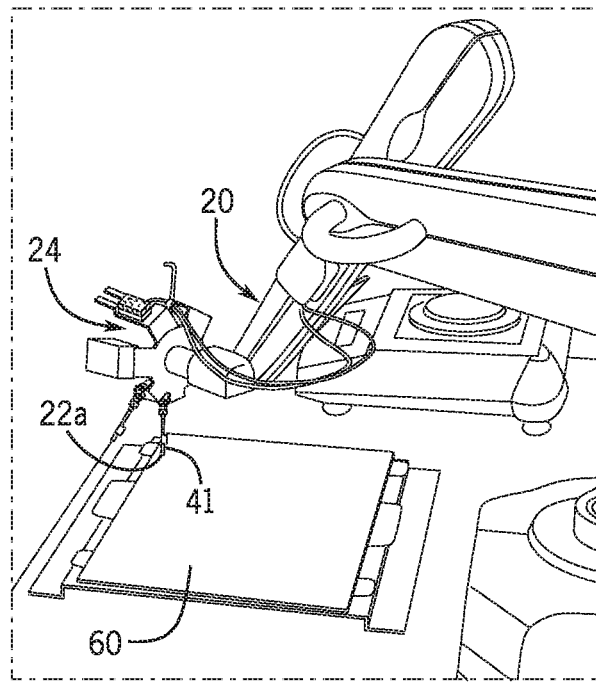
FIG. 25 is an enlarged perspective view of a different portion of the system shown in FIG. 2.

Finally, once the first gemstone 22*a* has been cleaned and analyzed at each desired processing station, the robotic arm 20 places the first gemstone 22*a* at a particular location on the holding plate 60, as shown in FIG. 25. In certain embodiments, any information stored by the system 10 in relation to the first gemstone 22*a* is then associated with the particular location on the holding plate 60 where that first gemstone is placed.

The second gemstone 22*b* is then taken to any desired additional processing stations and placed at a second particular location on the holding plate 60. The above process is further repeated for each of a plurality of the remaining gemstones 22 located in the initial repository 32. When it is desired to remove a particular gemstone from the system 10, the operator communicates to the system 10 an input associated with a particular location on the holding plate 60. For example, in certain embodiments, the operator could input a code into a touchscreen, key pad, bar code scanner, or other input mechanism capable of receiving a form of code input, the input corresponding to the particular gemstone, which the system knows is at a particular location on the holding plate 60. The robotic arm 20 then selects the particular gemstone from the corresponding particular location on the holding plate 60 and delivers the particular gemstone to the operator.

Although the invention has been herein described in what is perceived to be the most practical and preferred embodiments, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims and the description of the invention herein.

What is claimed is:

1. A gemstone handling and analysis system capable of cleaning and analyzing a series of gemstones, comprising:
   a platform;
   a plurality of stations, each positioned on the platform, the plurality of stations including:
      a gemstone repository having a ridged support surface and a slidable gemstone uprighting mechanism, positioned such that at least part of the gemstone uprighting mechanism slides over the support surface;
      a cleaning station for cleaning at least one side of each of at least some of the gemstones, the cleaning station having a rotatable cleaning stand capable of accepting a gemstone and a reservoir holding a gemstone cleaning solution;
      a gemstone imaging station having a gemstone imaging device capable of performing a light return analysis on a gemstone, a plate attached to the gemstone imaging device, the plate sized to receive a gemstone to be analyzed, and a removable cover capable of covering, at least in part, the plate; and
      a scale capable of weighing a gemstone;
      a gemstone color analyzer capable of determining a color grade for a gemstone;
      a gemstone clarity analyzer capable of determining a clarity grade for a gemstone;
      a gemstone origin analyzer capable of authenticating a gemstone; and
      a holding plate capable of holding gemstones in a particular location;
   a robotic arm connected to the platform, the robotic arm including:
      a gemstone gripper tool capable of selecting, moving, and depositing a gemstone;
      at least one tool capable of performing a cleaning function on at least one surface of a gemstone; and
   a plurality of external panels at least partially surrounding the platform and supported by a frame, at least one of the external panels being openable;
   a locking mechanism attached to one or more of the openable panels; and
   an input mechanism capable of receiving an input associated with a particular location on the holding plate and providing information to the robotic arm to select a gemstone positioned at the particular location on the holding plate.

2. A method of cleaning and analyzing a gemstone using a gemstone cleaning and analysis system including a platform and an automated positioning system connected to the platform, the method comprising:
   using the automated positioning system to select a gemstone from a plurality of gemstones;
   using the automated positioning system to deposit the gemstone onto a cleaning stand connected to the platform;
   using the automated positioning system to clean at least one side of the gemstone by rubbing at least one side of the gemstone with at least one cleaning tool;

using the automated positioning system to move the gemstone to a gemstone imaging device connected to the platform and having a plate, and to deposit the gemstone on the plate;

using the gemstone imaging device to identify the gemstone;

using the automated positioning system to move the gemstone to a holding plate connected to the platform and deposit the gemstone at a particular location of the holding plate.

3. A method of cleaning and analyzing a gemstone as in claim 2, wherein the rubbing of the gemstone is accomplished by rotating the cleaning stand while the automated positioning system moves the cleaning tool against a side of the gemstone.

4. A method of cleaning and analyzing a gemstone as in claim 2, further comprising the step of using the automated positioning system to wet at least one of the cleaning tools, in a reservoir connected to the platform and holding a gemstone cleaning solution, before the step of using the automated positioning system to rub the gemstone with the cleaning tool.

5. A method of cleaning and analyzing a gemstone as in claim 2, further comprising the steps of storing data related to the gemstone within the system and associating the stored data with the particular location where the gemstone is deposited on the holding plate.

6. A method of cleaning and analyzing a gemstone as in claim 2, further comprising the step of using the automated positioning system to retrieve the gemstone from the particular location on the holding plate in response to an input associated with the particular location on the holding plate.

7. A method of cleaning and analyzing a gemstone using a gemstone cleaning and analysis system including a platform and an automated positioning system connected to the platform, the method comprising:

using the automated positioning system to select a first gemstone from a plurality of gemstones;

using the automated positioning system to place the first gemstone onto a cleaning stand connected to the platform;

using the automated positioning system to clean at least one side of the first gemstone by rubbing at least one side of the first gemstone with at least one cleaning tool;

using the automated positioning system to remove, at least partially, a gemstone imaging device cover from a first gemstone imaging device connected to the platform, exposing at least part of a plate of the first gemstone imaging device;

using the automated positioning system to deposit the first gemstone onto the plate of the first gemstone imaging device;

using the automated positioning system to replace the gemstone imaging device cover of the first gemstone imaging device;

performing a light return analysis on the first gemstone, using the first gemstone imaging device;

using the automated positioning system to select a second gemstone from the plurality of gemstones;

using the automated positioning system to place the second gemstone onto the cleaning stand;

using the automated positioning system to clean the second gemstone by rubbing at least one side of the second gemstone with one or more polishing tools;

using the automated positioning system to remove, at least partially, a gemstone imaging device cover from a second gemstone imaging device connected to the platform, exposing at least part of a plate of the second gemstone imaging device;

using the automated positioning system to deposit the second gemstone onto the plate of the second gemstone imaging device;

using the automated positioning system to replace the gemstone imaging device cover of the second gemstone imaging device;

performing a light return analysis on the second gemstone, using the second gemstone imaging device;

using the automated positioning system to remove, at least partially, the gemstone imaging device cover of the first gemstone imaging device;

using the automated positioning system to move the first gemstone to a first location on a holding plate connected to the platform;

using the automated positioning system to remove, at least partially, the gemstone imaging device cover of the second gemstone imaging device; and using the automated positioning system to move the second gemstone to a second location on the holding plate.

* * * * *